United States Patent
Reddy et al.

(10) Patent No.: US 9,815,806 B2
(45) Date of Patent: Nov. 14, 2017

(54) PROCESS FOR CABAZITAXEL

(71) Applicant: HETERO RESEARCH FOUNDATION, Hyderabad (IN)

(72) Inventors: Bandi Parthasaradhi Reddy, Hyderabad (IN); Kura Rathnakar Reddy, Hyderabad (IN); Dasari Muralidhara Reddy, Hyderabad (IN); Adulla Venkat Narsimha Reddy, Hyderabad (IN); Bandi Vamsi Krishna, Hyderabad (IN)

(73) Assignee: Hetero Research Foundation (IN)

( * ) Notice: Subject to any disclaimer, the term of this patent is extended or adjusted under 35 U.S.C. 154(b) by 0 days.

(21) Appl. No.: 14/968,034

(22) Filed: Dec. 14, 2015

(65) Prior Publication Data

US 2017/0029392 A1 Feb. 2, 2017

Related U.S. Application Data

(63) Continuation of application No. PCT/IN2014/000395, filed on Jun. 12, 2014.

(30) Foreign Application Priority Data

Jun. 14, 2013 (IN) .......................... 2593/CHE/2013

(51) Int. Cl.
 *C07D 305/14* (2006.01)

(52) U.S. Cl.
 CPC .................. *C07D 305/14* (2013.01)

(58) Field of Classification Search
 CPC .................................... C07D 305/14
 USPC ....................... 549/510, 511, 215
 See application file for complete search history.

(56) References Cited

U.S. PATENT DOCUMENTS

5,847,170 A * 12/1998 Bouchard ............ C07D 305/14
549/510
5,962,705 A * 10/1999 Didier .................. C07D 305/14
548/215

FOREIGN PATENT DOCUMENTS

| CN | 102285947 | * 12/2011 |
| CN | 103421036 | * 12/2013 |
| WO | 2012/142117 | * 10/2012 |
| WO | 2013111157 | * 8/2013 |

* cited by examiner

*Primary Examiner* — Niloofar Rahmani
(74) *Attorney, Agent, or Firm* — Caesar Rivise, PC

(57) ABSTRACT

The present invention provides an improved process for the preparation of 4α-acetoxy-2α-benzoyloxy-5β,20-epoxy-1β,13α-dihydroxy-7β,10β-dimethoxy-9-oxo-11-taxene (7β,10β-dimethoxy-10-deacetoxybaccatin III). The present invention also provides a novel process for the preparation of cabazitaxel.

6 Claims, No Drawings

PROCESS FOR CABAZITAXEL

This application claims the benefit of Indian patent Application No. 2593/CHE/2013, filed on Jun. 14, 2013, which is incorporated herein by reference.

FIELD OF THE INVENTION

The present invention provides an improved process for the preparation of 4α-acetoxy-2α-benzoyloxy-5β,20-epoxy-1β,13α-dihydroxy-7β,10β-dimethoxy-9-oxo-11-taxene (7β,10β-dimethoxy-10-deacetoxybaccatin III). The present invention also provides a novel process for the preparation of cabazitaxel.

BACKGROUND OF THE INVENTION

Cabazitaxel is chemically, (2α,5β,7β,10β,13α)-4-acetoxy-13-({(2R,3S)-3[(tertbutoxycarbonyl)amino]-2-hydroxy-3-phenylpropanoyl}oxy)-1-hydroxy-7,10-dimethoxy-9-oxo-5,20-epoxytax-11-en-2-yl benzoate and has the structural formula:

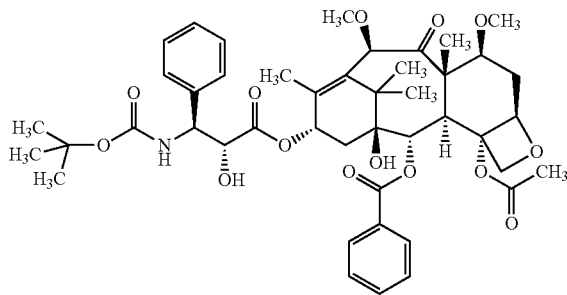 [SMILES: CO[C@H]1C(=O)[C@]2(C)[C@@H](OC)C[C@H]3OC[C@@]3(OC(C)=O)[C@H]2[C@H](OC(=O)c2ccccc2)[C@]2(O)C[C@H](OC(=O)[C@H](O)[C@@H](NC(=O)OC(C)(C)C)c3ccccc3)C(C)=C1C2(C)C]

Cabazitaxel is a drug for the treatment of hormone-refractory prostate cancer. It is marketed by Sanofi Aventis under the brand name JEVTANA®.

Cabazitaxel and its process were disclosed in U.S. Pat. No. 5,847,170 ('170 patent). According to '170 patent also described a process for the preparation of 4α-acetoxy-2α-benzoyloxy-5β,20-epoxy-1β,13α-dihydroxy-7β,10β-dimethoxy-9-oxo-11-taxene.

According to the '170 patent, cabazitaxel can be prepared by reacting 4α-acetoxy-2α-benzoyloxy-5β,20-epoxy-1β-hydroxy-7β,10β-dimethoxy-9-oxo-11-taxen-13α-yl(2R,4S,5R)-3-tert-butoxycarbonyl-2-(4-methoxyphenyl)-4-phenyl-1,3-oxazolidine-5-carboxylate with hydrochloric acid in ethanol.

U.S. Pat. No. 5,962,705 described a process for the preparation of 4α-acetoxy-2α-benzoyloxy-5β,20-epoxy-1β,13α-dihydroxy-7β,10β-dimethoxy-9-oxo-11-taxene can be prepared by reacting 4α-acetoxy-2α-benzoyloxy-5β,20-epoxy-1β,7β,10β,13α-tetrahydroxy-9-oxo-11-taxene with methyl iodide in the presence of sodium hydride and tetrahydrofuran, maintained for 7 hours 30 minutes and then poured into water and diisopropyl ether, and isolating.

U.S. patent application publication no. 2012/0149925 described a processes for the preparation of 4α-acetoxy-2α-benzoyloxy-5β,20-epoxy-1β,13α-dihydroxy-7β,10β-dimethoxy-9-oxo-11-taxene. According to the patent application also disclosed a process for the preparation of cabazitaxel can be prepared by reacting 1-hydroxy-7β,10β-di-methoxy-9-oxo-5β,20-epoxytax-11-ene-2α,4,13α-triyl-4-acetate-2-benzoate-13-{(2R,3S)-3-[(tert-butoxycarbonyl)amino]-2-triethylsilyloxy-3-phenylpropanoate} with hydrochloric acid in methanol and then quenched with sodium bicarbonate.

Processes for the preparation of 4α-acetoxy-2α-benzoyloxy-5β,20-epoxy-1β,13α-dihydroxy-7β,10β-dimethoxy-9-oxo-11-taxene were described in International patent application publication no. WO 2012/142117.

U.S. patent application publication no. 2013/090484 disclosed a process for the preparation of 4α-acetoxy-2α-benzoyloxy-5β,20-epoxy-1β,13α-dihydroxy-7β,10β-dimethoxy-9-oxo-11-taxen. According to the patent application also disclosed a process for the preparation of cabazitaxel.

4α-Acetoxy-2α-benzoyloxy-5β,20-epoxy-1β,13α-dihydroxy-7β,10β-dimethoxy-9-oxo-11-taxen (7β,10β-dimethoxy-10-deacetoxybaccatin III) is a key intermediate for the preparation of cabazitaxel.

We have found an improved process for the preparation of 7β,10β-dimethoxy-10-deacetoxybaccatin III. The process of the invention results in higher yields compared with the known process of using different solvent in the reaction.

We have also found a novel process for the preparation of cabazitaxel. The process of the present invention is simple, inexpensive, reproducible and is well suited on an industrial scale.

Thus, one object of the present invention is to provide an improved process for the preparation of 7β,10β-dimethoxy-10-deacetoxybaccatin III.

Another object of the present invention is to provide a novel process for the preparation of cabazitaxel.

SUMMARY OF THE INVENTION

In one aspect, the present invention provides an improved process for the preparation of 4α-acetoxy-2α-benzoyloxy-5β,20-epoxy-1β,13α-dihydroxy-7β,10β-dimethoxy-9-oxo-11-taxen (7β,10β-dimethoxy-10-deacetoxybaccatin III), which comprises:
  a) dissolving 4α-acetoxy-2α-benzoyloxy-5β,20-epoxy-1β,7β,10β,13α-tetrahydroxy-9-oxo-11-taxene (10-deacetylbaccatin III) in dimethylformamide, 2-methyltetrahydrofuran, N-methylpyrrolidone or mixture thereof;
  b) cooling the solution below 5° C.;
  c) adding sodium hydride to the reaction mass below 5° C.;
  d) adding methyl iodide to the reaction mass below 5° C.;
  e) maintaining the reaction mass below 5° C.;
  f) adding ester solvent to the reaction mass;
  g) separating out the organic layer; and
  h) concentrating the organic layer to obtain 7β,10β-dimethoxy-10-deacetoxybaccatin III.

In another aspect, the present invention provides an improved process for the preparation of cabazitaxel, which comprises:
  a) dissolving (2aR,4S,4aS,6R,9S,11S,12S,12aR,12bS)-12b-acetoxy-9-(((2R,3S)-3-amino-2-hydroxy-3-phenylpropanoyl)oxy)-11-hydroxy-4,6-dimethoxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-12-yl benzoate in an alcoholic solvent;
  b) adding di-tert-butyl dicarbonate to the solution;
  c) removing the solvent from the reaction mass to obtain a residual solid;
  d) adding chlorinated solvent, hydrocarbon solvent or nitrile solvent or mixture thereof to the residual solid; and
  e) isolating the cabazitaxel.

DETAILED DESCRIPTION OF THE INVENTION

The term "room temperature" refers to temperature at about 25 to 35° C.

According to one aspect of the present invention, there is provided an improved process for the preparation of 4α-acetoxy-2α-benzoyloxy-5β,20-epoxy-1β,13α-dihydroxy-7β,10β-dimethoxy-9-oxo-11-taxen (7β,10β-dimethoxy-10-deacetoxybaccatin III), which comprises:
a) dissolving 4α-acetoxy-2α-benzoyloxy-5β,20-epoxy-1β,7β,10β,13α-tetrahydroxy-9-oxo-11-taxene (10-deacetylbaccatin III) in dimethylformamide, 2-methyltetrahydrofuran, N-methylpyrrolidone or mixture thereof;
b) cooling the solution below 5° C.;
c) adding sodium hydride to the reaction mass below 5° C.;
d) adding methyl iodide to the reaction mass below 5° C.;
e) maintaining the reaction mass below 5° C.;
f) adding ester solvent to the reaction mass;
g) separating out the organic layer; and
h) concentrating the organic layer to obtain 7β,10β-dimethoxy-10-deacetoxybaccatin III.

The solution in step (b) may preferably be cooled to −15 to 3° C. and more preferably cooled to −10 to 0° C.

In step (e) the reaction mass may preferably be maintained for 1 to 2 hours.

The ester solvent used in step (f) may preferably be a solvent or a mixture of solvents selected from ethyl acetate, methyl acetate, isopropyl acetate, tert-butyl methyl acetate and ethyl formate, and more preferably the ester solvent is ethyl acetate.

Preferably the organic layer is concentrated in step (h) by distilling off the solvent. The distilling off the solvent may be carried out at atmospheric pressure or at reduced pressure. The distillation may preferably be carried out until the solvent is almost completely distilled off.

According to another aspect of the present invention, there is provided an improved process for the preparation of cabazitaxel, which comprises:
a) dissolving (2aR,4S,4aS,6R,9S,11S,12S,12aR,12bS)-12b-acetoxy-9-(((2R,3S)-3-amino-2-hydroxy-3-phenylpropanoyl)oxy)-11-hydroxy-4,6-dimethoxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-12-yl benzoate in an alcoholic solvent;
b) adding di-tert-butyl dicarbonate to the solution;
c) removing the solvent from the reaction mass to obtain a residual solid;
d) adding chlorinated solvent, hydrocarbon solvent or nitrile solvent or mixture thereof to the residual solid; and
e) isolating the cabazitaxel.

Preferably the alcoholic solvent used in step (a) may be a solvent or a mixture of solvents selected from methanol, ethanol, isopropyl alcohol and n-butanol, and more preferably the alcoholic solvent is methanol.

The solvent may be removed from the solution in step (c) by known methods, for example, distillation.

The distillation of the solvent may be carried out at atmospheric pressure or at reduced pressure. The distillation may preferably be carried out until the solvent is almost completely distilled off.

The chlorinated solvent used in step (d) may preferably be a solvent or a mixture of solvents selected from methylene chloride, chloromethane, ethylene chloride, chloroform, carbon tetrachloride and chlorobenzene. More preferably the chlorinated solvent is methylene chloride.

Preferably the hydrocarbon solvent used in step (d) may preferably be a solvent or a mixture of solvents selected from benzene, toluene, xylene, hexane, heptane, cyclopentane, cyclohexane, cyclohexene and cycloheptane. More preferably the hydrocarbon solvents are heptane and cyclohexane.

The nitrile solvent used in step (d) may preferably be a solvent or a mixture of solvents selected from acetonitrile, propionitrile, butyronitrile and benzonitrile, and more preferably the nitrile solvent is acetonitrile.

Cabazitaxel may be isolated in step (e) by methods known such as filtration or centrifugation.

The invention will now be further described by the following examples, which are illustrative rather than limiting.

EXAMPLES

Example 1

Preparation of 4α-acetoxy-2α-benzoyloxy-5β,20-epoxy-1β,13α-dihydroxy-7β,10β-dimethoxy-9-oxo-11-taxene (7β,10β-dimethoxy-10-deacetoxybaccatin III)

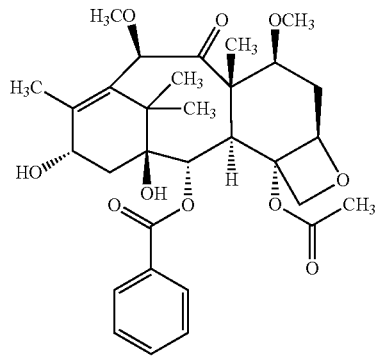 [SMILES: CO[C@H]1C(=O)[C@]2(C)[C@@H](OC)C[C@H]3OC[C@@]3(OC(C)=O)[C@H]2[C@H](OC(=O)c2ccccc2)[C@]2(O)C[C@H](O)C(C)=C1C2(C)C]

Dimethylformamide (100 ml) was added to 4α-acetoxy-2α-benzoyloxy-5β,20-epoxy-1β,7β,10β,13α-tetrahydroxy-9-oxo-11-taxene (20 gm) at room temperature and cooled to −10 to 0° C. Sodium hydride (3.7 gm) was added to the reaction mass and methyl iodide (60 ml) was then added. The reaction mass was stirred for 1 hour 30 minutes at −10 to 0° C. and ethyl acetate (100 ml) was added to the reaction mass. The layers were separated and aqueous layer was extracted with ethyl acetate. Combined organic layers were dried with sodium sulfate and then concentrated to obtain 10 gm of 7β,10β-dimethoxy-10-deacetoxybaccatin III.

Example 2

Preparation of 7β,10β-dimethoxy-10-deacetoxybaccatin III

To a 4α-acetoxy-2α-benzoyloxy-5β,20-epoxy-1β,7β,10β,13α-tetrahydroxy-9-oxo-11-taxene (10 gm) was added 2-methyltetrahydrofuran (50 ml) at room temperature and cooled to −10 to 0° C. To the reaction mass was added sodium hydride (2 gm) and methyl iodide (30 ml). The reaction mass was stirred for 2 hours at −10 to 0° C. and ethyl acetate (50 ml) was added to the reaction mass. The layers were separated and aqueous layer was extracted with ethyl acetate. Combined organic layers were dried with sodium sulfate and then concentrated to obtain 4.5 gm of 7β,10β-dimethoxy-10-deacetoxybaccatin III.

Example 3

Preparation of 7β,10β-dimethoxy-10-deacetoxybaccatin III
N-Methylpyrrolidone (60 ml) was added to 4α-acetoxy-2α-benzoyloxy-5β,20-epoxy-1β,7β,10β,13α-tetrahydroxy-9-oxo-11-taxene (10 gm) at room temperature and cooled to −10 to 0° C. Sodium hydride (2 gm) was added to the reaction mass and methyl iodide (30 ml) was then added. The reaction mass was stirred for 1 hour 30 minutes at −10 to 0° C. and ethyl acetate (50 ml) was added to the reaction mass. The layers were separated and aqueous layer was extracted with ethyl acetate. Combined organic layers were dried with sodium sulfate and then concentrated to obtain 4.5 gm of 7β,10β-dimethoxy-10-deacetoxybaccatin III.

Example 4

Preparation of 5-((2aR,4S,4aS,6R,9S,11S,12S,12aR,12bS)-12b-acetoxy-12-(benzoyloxy)-11-hydroxy-4,6-dimethoxy-4a,8,13,13-tetramethyl-5-oxo-2a,3,4,4a,5,6,9,10,11,12,12a,12b-dodecahydro-1H-7,11-methanocyclodeca[3,4]-benzo[1,2-b]oxet-9-yl)-3-(tert-butyl) (4S,5R)-2,2-dimethyl-4-phenyloxazolidine-3,5-dicarboxylate

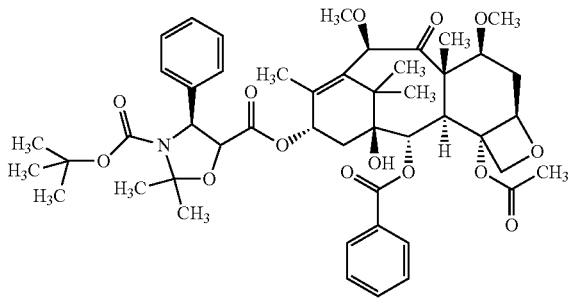 [SMILES: CO[C@H]1C(=O)[C@]2(C)[C@@H](OC)C[C@H]3OC[C@@]3(OC(C)=O)[C@H]2[C@H](OC(=O)c2ccccc2)[C@]2(O)C[C@H](OC(=O)C3OC(C)(C)N(C(=O)OC(C)(C)C)[C@H]3c3ccccc3)C(C)=C1C2(C)C]

7β,10β-Dimethoxy-10-deacetoxybaccatin III (22 gm), methylene chloride (660 ml), (4S,5R)-3-(tert-butoxycarbonyl)-2,2-dimethyl-4-phenyloxazoline-5-carboxylic acid (22 gm) and 4-(dimethylamino)pyridine (7 gm) were added at room temperature under stirring. To the reaction mixture was added N,N-dicyclohexylcarbodiimide (14 gm) and heated to 60° C. The reaction mass was stirred for 5 hours at 60° C. and methylene chloride (200 ml) was added to the reaction mass. The layers were separated and the aqueous layers were extracted with methylene chloride. Combined organic layers were dried with sodium sulfate to obtain a wet solid. To the wet solid was added hexane (500 ml) and methanol (5 ml) at room temperature. The contents were stirred for 14 hours at room temperature and filtered. The solid obtained was dried to obtain 28 gm of 5-((2aR,4S,4aS,6R,9S,11S,12S,12aR,12bS)-12b-acetoxy-12-(benzoyloxy)-11-hydroxy-4,6-dimethoxy-4a,8,13,13-tetramethyl-5-oxo-2a,3,4,4a,5,6,9,10,11,12,12a,12b-dodecahydro-1H-7,11-methanocyclodeca[3,4]-benzo[1,2-b]oxet-9-yl)-3-(tert-butyl) (4S,5R)-2,2-dimethyl-4-phenyloxazolidine-3,5-dicarboxylate.

Example 5

Preparation of (2aR,4S,4aS,6R,9S,11S,12S,12aR,12bS)-12b-acetoxy-9-(((2R,3S)-3-amino-2-hydroxy-3-phenylpropanoyl)oxy)-11-hydroxy-4,6-dimethoxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-12-yl benzoate Formic acid (600 ml) was added to 5-((2aR,4S,4aS,6R,9S,11S,12S,12aR,12bS)-12b-acetoxy-12-(benzoyloxy)-11-hydroxy-4,6-dimethoxy-4a,8,13,13-tetramethyl-5-oxo-2a,3,4,4a,5,6,9,10,11,12,12a,12b-dodecahydro-1H-7,11-methanocyclodeca[3,4]-benzo[1,2-b]oxet-9-yl)-3-(tert-butyl) (4S,5R)-2,2-dimethyl-4-phenyloxazolidine-3,5-dicarboxylate (50 gm) at 20° C. and stirred for 4 hours. The reaction mass was quenched with sodium chloride solution and stirred for 1 hour. The solution was extracted with methylene chloride. The organic layer was dried with sodium sulfate and then concentrated to obtain a solid. To the solid was added hexane (150 ml) and stirred for 2 hours. The separated solid was filtered and dried to obtain 35 gm of (2aR,4S,4aS,6R,9S,11S,12S,12aR,12bS)-12b-acetoxy-9-(((2R,3S)-3-amino-2-hydroxy-3-phenylpropanoyl)oxy)-11-hydroxy-4,6-dimethoxy-4a,8,13,13-tetramethyl-5-oxo-2a,3,4,4a,5,6,9,10,11,12,12a,12b-dodecahydro-1H-7,11-methanocyclodeca[3,4]-benzo[1,2-b]oxet-12-yl benzoate.

Example 6

Preparation of (2aR,4S,4aS,6R,9S,11S,12S,12aR,12bS)-12b-acetoxy-9-(((2R,3S)-3-amino-2-hydroxy-3-phenylpropanoyl)oxy)-11-hydroxy-4,6-dimethoxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-12-yl benzoate To a 5-((2aR,4S,4aS,6R,9S,11S,12S,12aR,12bS)-12b-acetoxy-12-(benzoyloxy)-11-hydroxy-4,6-dimethoxy-4a,8,13,13-tetramethyl-5-oxo-2a,3,4,4a,5,6,9,10,11,12,12a,12b-dodecahydro-1H-7,11-methanocyclodeca[3,4]-benzo[1,2-b]oxet-9-yl)-3-(tert-butyl) (4S,5R)-2,2-dimethyl-4-phenyloxazolidine-3,5-dicarboxylate (10 gm) was added trifluoroacetic acid (200 ml) at 20° C. and stirred for 4 hours. The reaction mass was quenched with sodium chloride solution and stirred for 1 hour. The solution was extracted with methylene chloride. The organic layer was dried with sodium sulfate and then concentrated to obtain a solid. To the solid was added methylene chloride (30 ml) and stirred for 2 hours. The separated solid was filtered and dried to obtain 6 gm of (2aR,4S,4aS,6R,9S,11S,12S,12aR,12bS)-12b-acetoxy-9-(((2R,3S)-3-amino-2-hydroxy-3-phenylpropanoyl)oxy)-11-hydroxy-4,6-dimethoxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-12-yl benzoate.

Example 7

Preparation of (2aR,4S,4aS,6R,9S,11S,12S,12aR,12bS)-12b-acetoxy-9-(((2R,3S)-3-amino-2-hydroxy-3-phenylpropanoyl)oxy)-11-hydroxy-4,6-dimethoxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-12-yl benzoate Acetic acid (150 ml) was added to 5-((2aR,4S,4aS,6R,9S,11S,12S,12aR,12bS)-12b-acetoxy-12-(benzoyloxy)-11-hydroxy-4,6-dimethoxy-4a,8,13,13-tetramethyl-5-oxo-2a,3,4,4a,5,6,9,10,11,12,12a,12b-dodecahydro-1H-7,11-methanocyclodeca[3,4]-benzo[1,2-b]oxet-9-yl)-3-(tert-butyl) (4S,5R)-2,2-dimethyl-4-phenyloxazolidine-3,5-dicarboxylate (10 gm) at 20° C. and stirred for 4 hours. The reaction mass was quenched with sodium chloride solution and stirred for 1 hour. The solution was extracted with methylene chloride. The organic layer was dried with sodium sulfate and then concentrated to obtain a solid. To the solid was added methanol (50 ml) and stirred for 2 hours. The separated solid was filtered and dried to obtain 6.5 gm of (2aR,4S,4aS,6R,9S,11S,12S,12aR,12bS)-12b-acetoxy-9-(((2R,3S)-3-amino-2-hydroxy-3-phenylpropanoyl)oxy)-11-hydroxy-4,6-dimethoxy-4a,8,13,13-tetramethyl-5-oxo-2a,3,4,4a,5,6,9,10,11,12,12a,12b-dodecahydro-1H-7,11-methanocyclodeca[3,4]-benzo[1,2-b]oxet-12-yl benzoate.

Example 8

Preparation Cabazitaxel (2aR,4S,4aS,6R,9S,11S,12S,12aR,12bS)-12b-acetoxy-9-(((2R,3S)-3-amino-2-hydroxy-3-phenylpropanoyl)oxy)-11-hydroxy-4,6-dimethoxy-4a,8,13,13-tetramethyl-5-oxo-2a,3,4,4a,5,6,9,10,11,12,12a,12b-dodecahydro-1H-7,11-methanocyclodeca[3,4]-benzo[1,2-b]oxet-12-yl benzoate (50 gm) was dissolved in methanol (750 ml) at room temperature under stirring and di-tert-butyl dicarbonate (22 ml) was then added slowly for 5 minutes. The reaction mass was stirred for 14 hours at room temperature and the methanol solvent was distilled off under reduced pressure to obtain a residual solid. To the residual solid was added methylene chloride (200 ml) to obtain a clear solution. The solution was dried with sodium sulfate and then concentrated to obtain a solid. To the solid was added a mixture of methylene chloride (200 ml) and cyclohexane (200 ml) and the contents were stirred for 5 hours. The separated solid was filtered and dried to obtain 40 gm of cabazitaxel.

Example 9

Preparation Cabazitaxel (2aR,4S,4aS,6R,9S,11S,12S,12aR,12bS)-12b-acetoxy-9-(((2R,3S)-3-amino-2-hydroxy-3-phenylpropanoyl)oxy)-11-hydroxy-4,6-dimethoxy-4a,8,13,13-tetramethyl-5-oxo-2a,3,4,4a,5,6,9,10,11,12,12a,12b-dodecahydro-1H-7,11-methanocyclodeca[3,4]-benzo[1,2-b]oxet-12-yl benzoate (5 gm) was dissolved in methanol (75 ml) at room temperature under stirring and di-tert-butyl dicarbonate (2 ml) was then added slowly for 5 minutes. The reaction mass was stirred for 14 hours at room temperature and the methanol solvent was distilled off under reduced pressure to obtain a residual solid. To the residual solid was added methylene chloride (20 ml) to obtain a clear solution. The solution was dried with sodium sulfate and then concentrated to obtain a solid. To the solid was added a mixture of acetonitrile (30 ml) and heptane (30 ml) and the contents were stirred for 5 hours. The separated solid was filtered and dried to obtain 3.5 gm of cabazitaxel.

We claim:

1. An improved process for the preparation of 4α-acetoxy-2α-benzoyloxy- 5β, 20-epoxy -1β, 13α- dihydroxy-7β, 10β-dimethoxy-9-oxo-11-taxen (7β, 10β-dimethoxy β10-deacetoxybaccatin III), which comprises:
   a. dissolving 4 α-acetoxy-2α-benzoyloxy-5β, 20-epoxy-1β,7β,10β,13α-tetrahydroxy-9-oxo-11-taxene (10-deacetylbaccatin III) in a solvent selected from dimethylformamide, 2-methyltetrahydrofuran, N-methylpyrrolidone or mixture thereof;
   b. cooling the solution below 5° C.;
   c. adding sodium hydride to the reaction mass below 5° C.;
   d. adding methyl iodide to the reaction mass below 5° C.;
   e. maintaining the reaction mass below 5° C.;
   f. adding ester solvent to the reaction mass;
   g. separating out the organic layer; and
   h. concentrating the organic layer to obtain 7β,10β-dimethoxy-10-deacetoxybaccatin III.

2. The process as claimed in claim 1, wherein the solution in step (b) is cooled to -15 to 3° C.

3. The process as claimed in claim 2, wherein the solution is cooled to -10 to 0° C.

4. The process as claimed in claim 1, wherein the ester solvent used in step (f) is a solvent or a mixture of solvents selected from ethyl acetate, methyl acetate, isopropyl acetate, tert-butyl methyl acetate and ethyl formate.

5. The process as claimed in claim 4, wherein the ester solvent is ethyl acetate.

6. The process of claim 1 wherein the reaction mass of step (e) is maintained for 1 to 2 hours.

\* \* \* \* \*